(12) United States Patent
Link

(10) Patent No.: US 8,241,361 B2
(45) Date of Patent: Aug. 14, 2012

(54) ENDOPROSTHESIS COMPONENT

(75) Inventor: Helmut D. Link, Hamburg (DE)

(73) Assignee: DERU GmbH, Norderstedt (DE)

(*) Notice: Subject to any disclaimer, the term of this patent is extended or adjusted under 35 U.S.C. 154(b) by 821 days.

(21) Appl. No.: 12/234,468

(22) Filed: Sep. 19, 2008

(65) Prior Publication Data

US 2009/0082849 A1  Mar. 26, 2009

Related U.S. Application Data

(60) Provisional application No. 60/973,940, filed on Sep. 20, 2007.

(51) Int. Cl.
*A61F 2/44* (2006.01)

(52) U.S. Cl. .................................................. 623/17.15

(58) Field of Classification Search ............... 623/17.15; 427/455, 456
See application file for complete search history.

(56) References Cited

U.S. PATENT DOCUMENTS

| | | | |
|---|---|---|---|
| 5,826,586 | A | 10/1998 | Mishra et al. |
| 2001/0036530 | A1 | 11/2001 | Noda et al. |
| 2004/0029692 | A1 | 2/2004 | Blair et al. |
| 2004/0246088 | A1 | 12/2004 | Shoji et al. |

FOREIGN PATENT DOCUMENTS

| | | |
|---|---|---|
| DE | 35 16 411 | 11/1986 |
| DE | 43 22 083 | 1/1995 |
| DE | 43 22 085 | 1/1995 |
| DE | 197 55 536 | 6/1999 |
| DE | 20 2005 005 405 | 6/2005 |
| EP | 0 421 084 | 4/1991 |
| EP | 0 633 440 | 1/1995 |
| EP | 1 440 669 | 7/2004 |
| EP | 1 580 292 | 9/2005 |
| EP | 1 674 051 | 6/2006 |
| JP | 2005-95584 | 4/2005 |
| JP | 2006-501867 | 1/2006 |
| WO | WO-99/30634 | 6/1999 |
| WO | WO-2009/036845 | 3/2009 |
| WO | WO-2010/015414 | 2/2010 |

*Primary Examiner* — Thomas Barrett
*Assistant Examiner* — Christine Nelson
(74) *Attorney, Agent, or Firm* — Morrison & Foerster LLP

(57) ABSTRACT

An endoprosthesis component is formed from a ceramic material and in which the ceramic material is partially coated with a titanium alloy. An uncoated surface portion of the endoprosthesis component is designed to interact as slide surface with another endoprosthesis component. A coated surface portion of the endoprosthesis component is designed to establish a connection to a bone. The part of the ceramic material forming an interface to the coating has a roughness $R_a$ of between 2.5 μM and 7 μM, creating a firm connection between the coating and the ceramic material. The invention further relates to a method for producing such an endoprosthesis component. To achieve the desired roughness of the surface, the ceramic component is presintered at a temperature of between 880° C. and 980° C. and is then treated with a blasting material.

17 Claims, 2 Drawing Sheets

ENDOPROSTHESIS COMPONENT

CROSS REFERENCE TO RELATED APPLICATIONS

This application claims priority to U.S. Provisional Application No. 60/973,940 filed Sep. 20, 2007, the contents of which are incorporated herein in their entirety.

FIELD OF THE INVENTION

The invention relates to an endoprosthesis component which is formed from a ceramic material and in which the ceramic material is partially coated with a titanium alloy. An uncoated surface portion of the endoprosthesis component is designed to interact as slide surface with another endoprosthesis component. A coated surface portion of the endoprosthesis component is designed to establish a connection to a bone. The invention further relates to a method for producing such an endoprosthesis component. The invention relates finally to a method for producing a ceramic component onto which the titanium alloy coating can be applied. In said method, a starting material in powder form is introduced into a mold that predefines the shape of the ceramic component. The ceramic component is then sintered in several steps.

Ceramic materials combine a high degree of mechanical strength and dimensional stability together with good biocompatibility. Ceramic materials are therefore used in the production of endoprostheses.

BACKGROUND OF THE INVENTION

In endoprostheses used to replace a joint, a stable connection must be established between the endoprosthesis and the bone structure. In this respect, ceramic materials are less advantageous than other materials, since their dense surface has the effect that connection to bone substance can be established only with difficulty. From WO 99/30634, it is known to apply a titanium alloy to coat the part of an endoprosthesis component that is intended to establish connection to bone substance. The coating has a greater porosity than the ceramic material. The bone substance can grow into the pores and in this way establish a stable connection to the endoprosthesis component.

The titanium alloy does not undergo chemical or metallurgical connection to the ceramic material. The connection between the titanium alloy and the ceramic material is thus a purely mechanical one. According to WO 99/30634, the titanium alloy should be applied to the ceramic material by plasma spraying. For a good mechanical connection, the surface of the ceramic material to be coated should be rough.

Tests have shown that a coating applied in this way does not establish a sufficiently stable connection to every rough surface. If the roughness $R_a$ is below 2 µm, the applied layer lifts from the ceramic material under loading.

SUMMARY OF THE INVENTION

An object of the invention is to propose an endoprosthesis component of the type described at the outset in which the coating adheres better to the ceramic material. It is also an object of the invention to propose a method for producing such a prosthesis and a method for producing a corresponding ceramic component. The objects are achieved by the features of the independent claims. Advantageous embodiments are set forth in the dependent claims. According to the invention, the part of the ceramic material forming an interface to the coating has a roughness $R_a$ of between 2.5 µm and 7 µm, preferably of between 3.5 µm and 5 µm.

A number of terms will first be described. The term roughness quantifies the unevenness of a surface. The roughness values within the context of the invention relate to the mean roughness $R_a$ according to DIN EN ISO 4288 and 3274.

The endoprosthesis component is formed from a ceramic material. The surface formed by the ceramic material is partially coated with a titanium alloy. The titanium coating does not necessarily form the outermost layer of the endoprosthesis component; rather, a further layer, for example made from a material which stimulates bone growth, may be applied to the titanium coating. A part of the surface is uncoated and designed to interact as slide surface with another endoprosthesis component. The uncoated area and the slide surface are not necessarily identical.

In the coated area, there is an interface between the ceramic material and the titanium alloy. The strength of the connection between the coating and the ceramic material is defined by the form of the ceramic material at the interface. Tests have shown that the connection between the coating and the ceramic material is insufficient if the roughness $R_a$ of the ceramic material at the interface is less than 2 µm. A good adherence is obtained starting from a roughness $R_a$ of 2.5 µm. The adherence is further improved if the roughness $R_a$ is greater than 3.5 µm.

It is desirable for the coating to be able to be applied in a single operation. If the roughness is too great, several layers have to be applied one after another to ensure that the ceramic surface is completely covered and that the layer thickness is sufficient everywhere. Therefore, the roughness $R_a$ of the ceramic material at the interface should not be greater than 7 µm, preferably not greater than 5 µm.

The FDA, the US licensing authority, stipulates that the adhesive pull strength, defined as per ASTM F1147, between the coating and the ceramic material must be at least 22 MPa. To observe a safety margin with respect to this limit, the adhesive pull strength between the coating and the ceramic material in the endoprosthesis component according to the invention should be at least 25 MPa, preferably at least 30 MPa, more preferably at least 40 MPa. The layer thickness of the coating, defined as per ASTM F1854, is preferably between 100 µm and 250 µm, preferably between 150 µm and 200 µm.

A good connection between the bone substance and the coating is achieved if the coating has the following properties. The pore proportion, defined as per ASTM F1854, is between 20% and 40%. The pore width, also defined as per ASTM F1854, is between 30 µm and 70 µm, preferably between 40 µm and 60 µm.

Zirconium oxide, aluminum oxide, and mixtures of the two, have proven suitable as ceramic materials for the endoprosthesis component according to the invention. The term "titanium alloy" comprises pure titanium.

The endoprosthesis component is preferably one of several components of an intervertebral disk prosthesis. The part designed as slide surface forms the slide surface of the intervertebral disk prosthesis.

The method according to the invention for producing an endoprosthesis component involves first selecting a suitably formed ceramic structural part in which the surface to be coated has a roughness $R_a$ of between 2.5 µm and 7 µm, preferably of between 3.5 µm and 5 µm. A titanium alloy is applied by plasma spraying to the surface to be coated. Plasma spraying is a method in which a gas is conveyed through an electric arc and is thereby ionized. The coating material is introduced in powder form into the ionized gas and is transported by the stream of gas onto the workpiece that is to be coated.

It has been found that the production of a ceramic component in which a surface to be coated has a roughness $R_a$ of between 2.5 μm and 7 μm is not an entirely simple matter. In the conventional production methods, the surface roughness is much less, and it is not easy to subsequently provide the ceramic component with a greater degree of roughness. To produce ceramic components, a ceramic starting material in the form of a powder is first introduced in a mold that predefines the shape of the ceramic component. Since the volume of the ceramic component decreases in the subsequent working steps, the mold is larger than the finished ceramic component. A stable inner structure of the ceramic component is achieved by subsequent sintering. The sintering results in formation of firm connections between the particles of the powder.

The sintering is carried out in several steps. In a first step, the ceramic component is presintered at a lower temperature, such that only narrow bridges form between the grains of the powder. The ceramic component can be worked mechanically in the presintered state. On the one hand, the inner structure is so firm that the ceramic component retains its shape despite the mechanical action. On the other hand, the bridges are so easily broken up again that the material can be worked relatively easily. The higher the presintering temperature that is chosen, the more stable the bridges and, consequently, the more difficult the mechanical working. The presintering temperature is therefore chosen as low as possible to ensure that the bridges have just enough stability to keep the ceramic component in its shape. Ceramic components made of zirconium oxide ($ZrO_2$) and aluminum oxide ($Al_2O_3$) are usually presintered at temperatures of below 850° C. prior to the mechanical working. Typical steps in the mechanical working are drilling and milling. There are no known mechanical working steps with which the roughness $R_a$ of the surface can subsequently be increased to values of between 2.5 μm and 7 μm.

According to the invention, the ceramic component is presintered at a temperature of between 880° C. and 980° C., preferably between 900° C. and 950° C. The surface of the ceramic component is then treated with a blasting material. Tests have shown that, in the case of a component that has been presintered at this temperature, the treatment with a blasting material leads to the desired surface roughness. The inner structure of the ceramic component after the presintering is therefore exactly such that fragments of the desired size can be broken out of the component with the blasting material.

In the endoprosthesis component according to the invention, only part of the surface is coated, while another part of the surface is designed to interact as slide surface with another endoprosthesis component. The surface roughness should be as low as possible on the slide surface. If a surface is to be obtained that is as smooth as possible, it is not desirable to increase the roughness of the surface beforehand by treatment with a blasting material. Preferably, therefore, only part of the surface of the ceramic component is treated with the blasting material, while another part of the surface remains excluded from the treatment with the blasting material.

The particle size of the blasting material is preferably of the same order of magnitude as the particle size of the ceramic starting material. The blasting material can then act particularly effectively on the ceramic component. However, when using such a blasting material, there is the danger of particles of the blasting material settling in the interstices that are formed in the ceramic material when the fragments are ejected. The particles then constitute impurities in the ceramic material. Impurities of this kind can be avoided by using, as blasting material, a powder that corresponds to the powder of the ceramic starting material. If particles of this material settle in the ceramic component, they do not in any way change the homogeneous composition of the ceramic material.

BRIEF DESCRIPTION OF THE DRAWINGS

The invention is described in more detail below with reference to the attached drawing and on the basis of an advantageous illustrative embodiment. In the drawing.

DETAILED DESCRIPTION OF THE INVENTION

Figure 1:
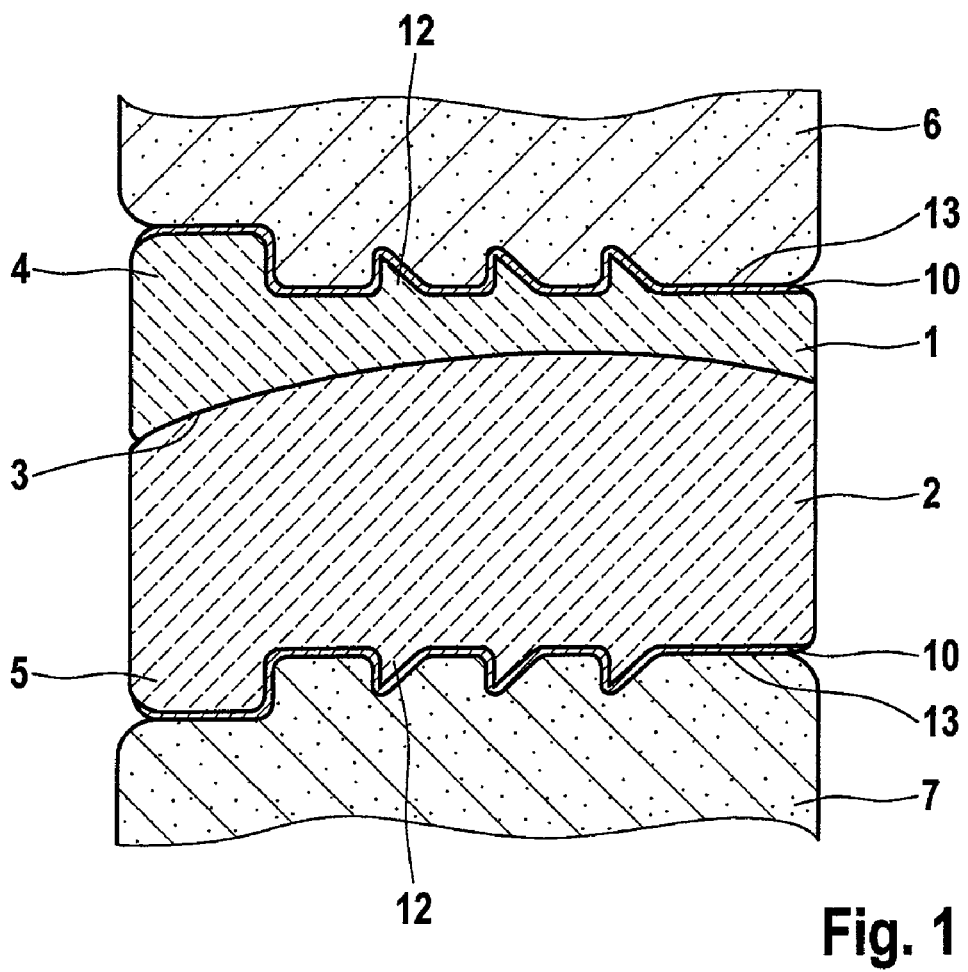
FIG. 1 shows an intervertebral disk prosthesis in cross section.

In FIG. 1, an endoprosthesis designed as an intervertebral disk prosthesis is inserted into an intervertebral space between two vertebral bodies 6, 7. The intervertebral disk prosthesis comprises a first contact plate 1 and a second contact plate 2. The first contact plate 1 is an endoprosthesis component designed for connection to a first vertebral body 6, and the second contact plate 2 is an endoprosthesis component designed for connection to a second vertebral body 7.

The first contact plate 1 and the second contact plate 2 bear on each other via matching slide surfaces 3. The slide surfaces 3 form a hinge for movements between the upper contact plate 1 and the lower contact plate 2.

Projections 12 are formed in areas 13 of the surfaces of the contact plates 1, 2 at which the contact plates 1, 2 bear on the bone substance of the vertebral bodies 6, 7. The projections 12 have a shallower flank in the direction in which the contact plates 1, 2 are pushed into the intervertebral space, and a steeper flank in the opposite direction. The shallower flank makes it easier to push the contact plates 1, 2 into the intervertebral space. The steeper flank provides the contact plates 1, 2 with a hold when the projections 12 have penetrated into the bone substance of the vertebral bodies 6, 7. The steeper flanks prevent the contact plates 1, 2 from being pulled back out again from the intervertebral space in the opposite direction.

Flanges 4, 5 of the contact plates 1, 2 are intended to bear on the ventral aspect of the vertebral bodies 6, 7. The flanges 4, 5 have the effect that the contact plates 1, 2 cannot be pushed into the intervertebral space in the dorsal direction any further than the desired position.

The contact plate 1 and the contact plate 2 are formed from a ceramic material 9. The slide surfaces 3 on the contact plates 1, 2 are formed on a surface of the ceramic material 9. The areas 13 at which a connection to the bone substance is established are coated with a titanium alloy coating 10.

Figure 2:
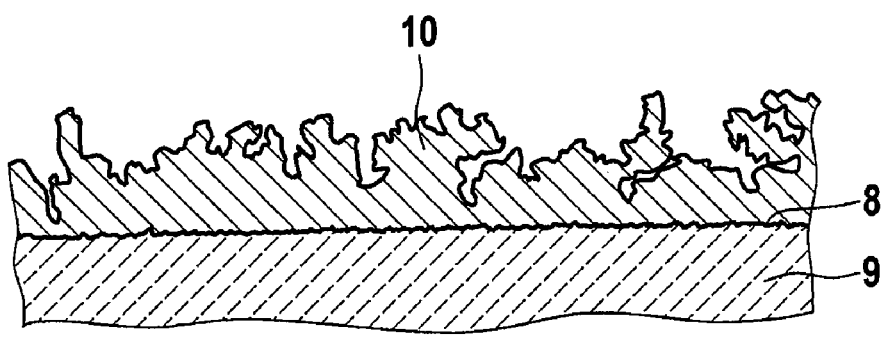
FIG. 2 shows an enlarged detail of the intervertebral disk prosthesis according to FIG. 1.

FIG. 2 shows an enlarged detail of a contact plate 1, 2, in which the interface 8 between the ceramic material 9 and the coating 10 is shown. The ceramic material 9 has a roughness $R_a$ of at least 2.5 μm at the interface 8 to the coating 10. This roughness at the interface 8 is sufficient to establish a stable connection to the coating 10, but it is not sufficient for a stable connection to bone substance. The coating 10 has a greater roughness and greater porosity than the ceramic material 9 and thus forms a stable connection to the bone substance.

Figure 3:
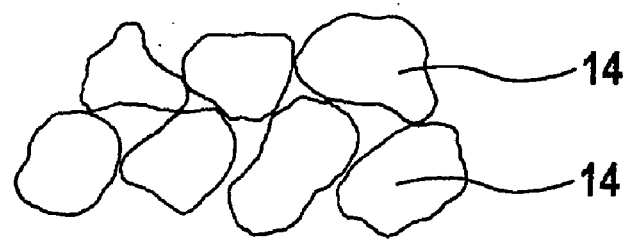
FIG. 3 shows a schematic illustration of the internal structure of the ceramic material in the starting state.
Figure 4:
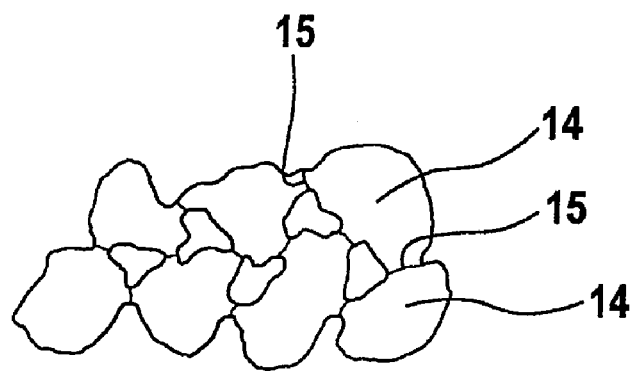
FIG. 4 shows the view from FIG. 3 after the presintering.
Figure 5:
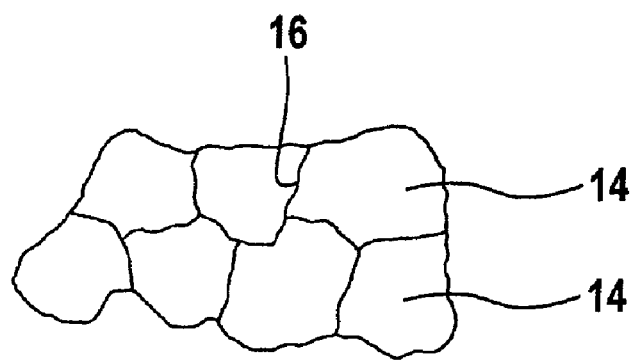
FIG. 5 shows the view from FIG. 3 after the sintering.

In order to produce a ceramic component in the form of an endoprosthesis component in which part of the surface has the desired roughness, a starting material in powder form is first introduced into a mold whose shape corresponds to the ceramic component that is to be produced. Since the ceramic component loses volume in the subsequent method steps, the mold has greater dimensions than the finished ceramic component. The powder is mechanically compacted in the mold, for example by vibration and pressure, after which the particles 14 of the powder lie alongside one another as is shown schematically in FIG. 3. As a result of the presintering at a temperature of 920° C., bridges, shown in FIG. 4, form between the particles 14. The inner structure of the material is now so stable that the ceramic component can be removed from the mold.

With the bridges 15, the ceramic material has a greater stability of its structure than would be chosen for mechanical working by drilling or milling. The stability of the structure is set precisely such that fragments can be detached from the presintered ceramic material by blasting with a powder that corresponds to the starting material. The fragments are of such a size that the desired surface roughness is obtained.

When the desired surface structure is achieved and the mechanical working is concluded, the ceramic component is sintered at a temperature higher than the presintering temperature. Planar connections 16 form at the interfaces of the particles, which have hitherto been connected only by the bridges 15. Since the cavities disappear from the inside, the volume of the ceramic component decreases further. On the part of the surface that was treated with the blasting material, the surface now has a roughness $R_a$ of approximately 4 μm. A titanium alloy coating applied to this surface portion adheres firmly to the surface.

The invention claimed is:

1. An endoprosthesis component which is formed from a ceramic material and in which the ceramic material is partially coated with a titanium alloy, an uncoated surface portion being designed to interact as a slide surface with another prosthesis component, and a coated surface portion being designed for connection to a bone, wherein the part of the ceramic material forming an interface to the coating has a roughness $R_a$ of between 2.5 μm and 7 μm.

2. The endoprosthesis component as claimed in claim 1, wherein the adhesive pull strength between the coating and the ceramic material is greater than 25 MPa.

3. The endoprosthesis component as claimed in claim 2, wherein the surface of the coating has a roughness $R_a$ of between 20 μm and 30 μm.

4. The endoprosthesis component as claimed in claim 2, wherein the surface of the coating has a roughness $R_a$ of between 15 μm and 35 μm.

5. The endoprosthesis component as claimed in claim 4, wherein the layer thickness of the coating is between 150 μm and 200 μm.

6. The endoprosthesis component as claimed in claim 5, wherein the pore width of the coating is between 40 μm and 60 μm.

7. The endoprosthesis component as claimed in claim 6, wherein the ceramic material comprises zirconium oxide and/or aluminum oxide.

8. The endoprosthesis component as claimed in claim 4, wherein the layer thickness of the coating is between 100 μm and 250 μm.

9. The endoprosthesis component as claimed in claim 8, wherein the proportion of the coating taken up by pores is between 20% and 40%.

10. The endoprosthesis component as claimed in claim 9, wherein the pore width of the coating is between 30 μm and 70 μm.

11. The endoprosthesis component as claimed in claim 10, wherein the ceramic material comprises zirconium oxide and/or aluminum oxide.

12. The endoprosthesis component as claimed in claim 11, wherein the part of the ceramic surface designed as slide surface is intended to form a slide surface of an intervertebral disk prosthesis.

13. The endoprosthesis component as claimed in claim 1, wherein the part of the ceramic material forming an interface to the coating has a roughness $R_a$ of between 3.5 μm and 5 μm.

14. The endoprosthesis component as claimed in claim 1, wherein the adhesive pull strength between the coating and the ceramic material is greater than 30 MPa.

15. The endoprosthesis component as claimed in claim 1, wherein the adhesive pull strength between the coating and the ceramic material is greater than 40 MPa.

16. A method for producing the endoprosthesis component as claimed in claim 12, comprising:
   a. selecting a ceramic structural part which has been formed as an endoprosthesis component and in which a surface to be coated has a roughness $R_a$ of between 2.5 μm and 7 μm, and
   b. applying a titanium alloy coating, by means of plasma spraying, to the surface to be coated.

17. The method as claimed in claim 16, wherein the coating is applied in one operation.

* * * * *